United States Patent [19]

Brown et al.

[11] Patent Number: 4,703,069
[45] Date of Patent: Oct. 27, 1987

[54] POLYETHER POLYOLS, THEIR MANUFACTURE AND USE IN POLYURETHANES PRODUCTION

[75] Inventors: James P. Brown, Sterrebeek; Ronald N. May, Brussels; David Randall, Erps Kwerps, all of Belgium

[73] Assignee: Imperial Chemical Industries plc, London, England

[21] Appl. No.: 879,435

[22] Filed: Jun. 27, 1986

[30] Foreign Application Priority Data

Jul. 1, 1985 [GB] United Kingdom ............. 8516618

[51] Int. Cl.$^4$ ............................................. C08G 18/14
[52] U.S. Cl. .................................. 521/174; 252/182; 521/176; 549/374; 568/619; 568/623; 568/624
[58] Field of Search ............... 521/174, 176; 549/374; 568/619, 623, 624; 252/182

[56] References Cited

U.S. PATENT DOCUMENTS 3,290,387 12/1966 Bernardy et al. ............... 568/623

Primary Examiner—Maurice J. Welsh
Attorney, Agent, or Firm—Cushman, Darby & Cushman

[57] ABSTRACT

This invention relates to polyether polyols having an average hydroxyl value in the range of 100 to 250 mgKOH/g, which are alkoxylated derivatives of a polyhydric alcohol being a mixture of compounds according to formula (I) or/and (II)

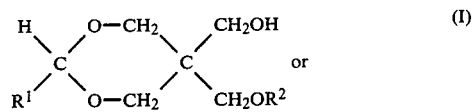

or

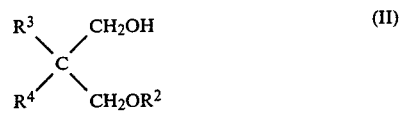

wherein
$R^1$ is H, $CH_3$ or $OCH_3$,
$R^2$ is H, $CH_2OH$ or $CH_2 C(CH_2OH)_3$, and
$R^3$ and $R^4$ are
H, $CH_2OH$ or $CH_2OCH_3$.

9 Claims, No Drawings

POLYETHER POLYOLS, THEIR MANUFACTURE AND USE IN POLYURETHANES PRODUCTION

The present invention relates to new alkoxylated derivatives of certain polyhydric alcohols and their use as compatibilising agent in the manufacture of polyurethanes, more particularly rigid polyurethane foams.

When the components of rigid polyurethane foam are mixed there is a tendency for the polyol component to separate from the isocyanate component, polymeric MDI for example, due to physical incompatibility. Under conditions of high mixing efficiency (i.e. impingement under high pressure, 200 bar for example, or mixing under high shear) polymerisation and foaming occurs before separation can take place.

However, under conditions of low mixing efficiency (i.e. low shear) often encountered in large scale production, the rigid foams produced have areas rich in polyol and areas rich in isocyanate. Under very low shear with badly mixing components the actual polymerisation reaction may be impaired. Using a laboratory variable shear mixer the behaviour of commercial systems may be investigated and the above conclusions can be substantiated.

It has now been observed, quite surprisingly, that the addition of a small amount of a defined polyether polyol derived from the polyalkoxylation of a by-product of pentaerythritol manufacture, from formaldehyde and acetaldehyde, behaves as a compatibilising agent for certain polyols with polyisocyanates.

Known compatibilising agents are based on expensive glycerol derivatives.

The cheap and readily available pentaerythritol residues are a mixture of pentaerythritol and pentaerythritol derivatives comprising formaldehyde derived acetals according to the general formula (I)

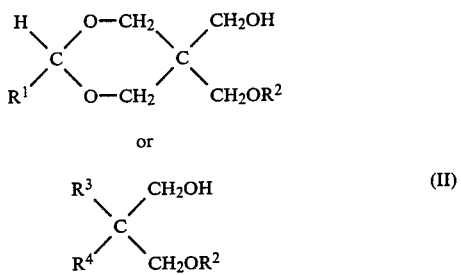

where $R^1$ is —H, —CH$_3$ or —OCH$_3$
$R^2$ is —H, —CH$_2$OH or —CH$_2$C(CH$_2$OH)$_3$
$R^3$ and $R^4$, which may be the same or different, are —H CH$_2$OH, —OCH$_2$C(CH$_2$OH)$_3$.

These pentaerythritol by-products and alkoxylated derivatives thereof are further described in British Patent Application No. 8404022. This patent application discloses polyether polyol having an average hydroxyl value in the range 400–650 mgKOH/g which is a mixture of alkoxylated derivatives of compounds of formula I and II.

British Patent Application No. 85 04096 describes polyester polyols derived from such polyether polyol.

The polyhydric alcohol according to formula (I) and (II) is used as an initiator for alkoxylation with an alkylene oxide, such as propylene oxide, ethylene oxide, butylene oxide or mixtures of two or more alkylene oxides. Alkoxylation may take place sequentially with different alkylene oxides.

The preferred polyether polyols of the invention are derived from propylene oxide and ethylene oxide.

A method of oxalkylation to afford the defined polyether polyol of the invention is known and is described in detail in the examples 1 and 5. Other methods well-known to the man skilled in the art may also be used. The above mentioned by-products should be oxyalkylated to a hydroxyl value in the range of 100 to 250 mg KOH/g, most preferably 125 to 175 mg KOH/g. The amount of the polyether polyol of the present invention to be added to the main polyol blend is in the range of 1 to 20 parts on 100 parts of polyol, most preferably 5 to 15 parts. The use of the resulting polyol blend for rigid foam manufacture is given in the examples A to E and the benefits are described.

The main polyol blend to which the polyol of the invention is added preferably consists of one or more polyether polyol based for example on sucrose, sorbitol, glycerol, bisphenol A, alkanolamine, toluene diamine, polyalkylenepolyamine or mixtures thereof, oxyalkylated to a hydroxyl value ranging from 200 to 600 mgKOH/g. The polyol blend may also be a polyester polyol or a mixture of polyether and polyester polyols.

The present invention includes the manufacture of polyurethane products, for example polyurethane foams, in known manner, from the polyether and polyester polyols described above to which the polyol of the invention has been added, and also includes polyurethane products so prepared. Polyurethane products are made by reacting a di- or polyisocyanate with the described polyether and polyester polyols. The nature of the polyurethane product, for example the polyurethane foam may be varied depending on a variety of factors such as the functionality of the reactants and the presence of active ingredients.

The organic di- or polyisocyanates may be any of the isocyanates known to be useful for the formation of polyurethane products such as polyurethane foams. Of particular interest are aromatic di- or polyisocyanates, for example tolylene diisocyanate and especially diphenylmethane diisocyanate (MDI) which are commercialy available in a variety of forms. Suitable diphenylmethane di-isocyanates include:

(a) diphenylmethane 4,4' diisocyanate and mixtures thereof with other isomers of diphenylmethane diisocyanate;

(b) methylene bridged polyphenylpolyisocyanates prepared by phosgenation of mixtures of appropriate polyamines obtained by the condensation of aniline and formaldehyde and known as 'polymeric' MDI, the composition of which may subsequently be varied by distillation, crystallisation or other separation techniques to give products with a weight average functionality in the range 2 to at least 3.3 ;

(c) polymers and oligomers obtained by reacting diphenylmethane diisocyanates or polymeric MDI with a monomeric glycol or polyhydric alcohol (or mixtures thereof) or with a hydroxyl-ended polyester or polyether and known as 'MDI prepolymers'; and (d) modified diphenylmethane diisocyanates or 'polymeric MDI' in which a proportion of the isocyanate groups are converted into other groups such as carbodiimide, uretoneimine, biuret or allophanate groups, or in which a proportion of the isocyanate groups are reacted with an isocyanate-reactive compound.

The preparation of the foamed polyurethane materials may be carried out by the general methods fully described elsewhere. Thus the foam forming components may be mixed continuously or discontinuously in the presence of the gas generating agent to give a foam. The foam forming gas may be generated by a variety of methods. For example the gas may be carbon dioxide generated by the reaction of a proportion of the organic isocyanate with water incorporated in the reaction mixture. Gas may also be generated by incorporating in the reaction mixture an inert liquid of low boiling point which vaporises during the exothermic polyurethane foaming reaction. Mixtures of water with inert low boiling point liquids may be used if desired.

Suitable inert low-boiling point liquids are liquids that are inert towards the polyurethane foam forming ingredients and have boiling point not exceeding 75 deg C. at atmospheric pressure and preferably between −40 deg C. and 50 deg C. Examples of such liquids are halogenated hydrocarbons such as methylene chloride, trichloromonofluoromethane, dichlorodifluoromethane, dichloromonofluoromethane, monochlorodifluoromethane, dichlorotetrafluoroethane, 1,1,2-trichlor-1,2,2-trifluoroethane, dibromofluoromethane and monobromotrifluoromethane. Mixtures of these low boiling liquids one with another and/or with other substituted or unsubstituted hydrocarbons may also be used. Such liquids are usually employed in amounts of from 1% to 100%, preferably 5% to 35% by weight of the polyol.

It is generally preferred to carry out the foam preparation in a single stage reaction of the organic polyisocyanate with the polyol in the presence of gas-generating agent.

If desired there may also be included in the polyurethane forming reaction mixture a catalyst. Suitable catalysts are well known in the art and include basic compounds of all types but particularly tertiary amines. Examples of suitable tertiary amines include triethylamine, dimethyl cycohexylamine, dimethylbenzylamine, dimethylphenylethylamine, tetramethyl-1,3-butanediamine, triethylene diamine, N-alkyl morpholines, N-alkylpyrrolidines and fully N-substituted 4-aminopyridines such as 4-dimethylaminopyridine, and bis (2-dimethylaminoethyl)ether.

Other suitable catalysts include basic and non-basic organic compounds of metals, for example dibutyltin dilaurate, manganese acetylacetonate, stannous carboxylates such as stannous octoate. Mixtures of catalysts are often particularly advantageous. As described in the prior art, the general methods of preparation of foamed polyurethane may include the incorporation in the polyurethane forming mixture of various additives such as surface-active agents. Suitable surface active agents include silicone fluids and particularly siloxane-oxyalkylene block copolymers. Oxyethylated phenols, oxyethylated fatty alcohols and block copolymers of ethylene and propylene oxides are examples of other surface-active agents which may be employed.

The polyurethane forming reaction may further be modified by the inclusion of known additives such as fillers, plasticisers, flame-retardants such as tris(beta-chloroethyl)phosphate, tris(beta-chloroisopropyl)phosphate or antimony oxide and antioxidants.

The resulting polyurethane foams and articles made thereof are also within the scope of the present invention.

The invention is illustrated but not limited by the following examples in which all parts and percentages are by weight.

EXAMPLE 1

Production of the polyether polyol of the invention. X parts of pentaerythritol residues having a hydroxyl value of 796 mgKOH/g and containing 0.24% sodium formate is charged to a stainless steel reactor and purged well with nitrogen. This residue is a mixture of polyhydric alcohols as follows:

| | |
|---|---|
| 5-(5-hydroxy methyl-1,3-dioxane)-methanol | 58.6% |
| 5-(5-hydroxy methyl-1,3-dioxane)-methoxy-methanol | 8.1% |
| pentaerythritol | 9.4% |
| pentaerythritol monohydroxymethylether | 8.7% |
| other polyhydric alcohols according to either of formula I and II each individually present at less than 3% totalling, | 15.2% |

Water and other volatiles are removed by heating to 150 deg C. with agitation under reduced pressure. Y parts of propylene oxide is added over 7 hours, maintaining the temperature at 150-160 deg C. and allowing the pressure to rise to a maximum of 4.5 bar absolute. On completion of the addition the reaction is allowed to continue until the pressure remains constant. The residual propylene oxide is removed by applying vacuum, and maintaining the temperature at 150-160 deg C. for 30 min.

9100 parts of the resulting polyol A cooled to 40 deg C. is treated with 1000 parts of water, and passed through an acid ion-exchange resin at 40 deg C. The water is then removed under reduced pressure at 110 deg C. until the water content is less than 0.1%

The obtained products 1a, 1b, 1c and 1d have a hydroxyl value, an acid value and a viscosity at 25 deg. Celsius as stated in Table I.

TABLE I

| Example | X | Y | hydroxyl mgKOHg$^{-1}$ | acid value mgKOHg$^{-1}$ | viscocity centistokes |
|---|---|---|---|---|---|
| 1a | 3501 | 15886 | 155 | 0.1 | 384 |
| 1b | 2870 | 7130 | 245 | — | — |
| 1c | 2870 | 21,639 | 105 | 0.1 | 354 |
| 1d | 2343 | 7654 | 205 | 0.03 | 410 |

EXAMPLE 2

8198 parts of untreated polyol product 1 a of example 1 is neutralised with 11.4 parts of 85% phosphoric acid solution diluted with 425 parts of water, at 80 deg C. The water is removed slowly under reduced pressure allowing the temperature to rise to 120 deg C. When the water content is less than 0.1% the material is passed through a heated Calmic filter to remove the precipitated phosphate salt. The product has a hydroxyl value of 152 mg KOH/g, an acid value of 0.26 mgKOH/g, a water content of 0.025%, a viscosity at 25 deg C. of 356 centistokes and a sodium content of 4 ppm.

EXAMPLE 3

5497 parts of the untreated polyol product 1b of example 1 having a hydroxyl value of 245 mgKOHg$^{-1}$ is charged to a stainless steel reactor and purged well with nitrogen. A nitrogen pressure of 1 bar gauge is applied to the reaction vessel. The temperature is raised to 120 deg. Celsius and 3603 parts of ethylene oxide are added with agitation, over a period of 4 hours. On completion of the addition the reaction is allowed to continue until the pressure remains constant. The residual ethylene oxide is removed by applying vacuum at 120 deg. Celsius for 30 min. 8100 parts of the resulting polyol cooled to 40 deg. Celsius is treated with 1000 parts of water, and passed through an acid ion exchange resin at 40 deg. Celsius. The water is then removed under reduced pressure at 110 deg. Celsius until the water content is less than 0.1%. The product 3 has a hydroxyl value of 150 mg KOHg$^{-1}$, a water content of 0.02%, an acid value of 0.07 mgKOHg$^{-1}$ and a viscosity of 267 centistokes.

EXAMPLE 4

2912 parts of the pentaerythritol residues of example 1 is charged to a stainless steel reactor and purged with nitrogen. Water and other volatiles are removed by heating to 120 deg. Celsius with agitation under reduced pressure for 1 hour. At a temperature of 120 deg. Celsius a pressure of 1 bar gauge of nitrogen is applied to the reactor and ethylene oxide is added. 13,545 parts of ethylene oxide is added with agitation in 6½ hours. On completion of the addition the reaction is allowed to continue until the pressure remains constant. The residual ethylene oxide is removed by applying vacuum at 120 deg. Celsius for 30 min. 8100 parts of the resulting polyol cooled to 40 deg. Celsius is treated with 1000 parts of water and passed through as acid ion exchange resin at 40 deg. Celsius. The water is then removed under reduced pressure at 110 deg. Celsius until the water content is less than 0.1%. The product 4 has a hydroxyl value of 150 mgKOHg$^{-1}$, a water content of 0.02%, an acid value of 0.06 mgKOHg$^{-1}$ and a viscosity of 305 centistokes.

EXAMPLE 5

2912 parts of the pentaerythritol residues of example 1 is charged to a stainless steel reactor and purged with nitrogen. Water and other volatiles are removed by heating to 120 deg. Celsius with agitation under reduced pressure for 1 hour. At a temperature of 120 deg. Celsius, a pressure of 1 bar gauge of nitrogen is applied to the reaction and ethylene oxide is added. 6872 parts of ethylene oxide is added with agitation in 6½ hours. On completion of the addition the reaction is allowed to continue until the pressure remains constant. The residual ethylene oxide is removed by applying vacuum at 120 deg. Celsius for 30 min. 6674 parts of propylene oxide is added over 7 hours, maintaining the temperature at 150–160 deg. Celsius and allowing the pressure to rise to a maximum of 4.5 bar absolute. On completion of the addition the reaction is allowed to continue until the pressure remains constant. The residual propylene oxide is removed by applying vacuum, and maintaining the temperature at 150–160 deg Celsius for 30 min. 9100 parts of the resulting polyol cooled to 40 deg. Celsius is treated with 1000 parts of water and passed through an acid ion exchange resin at 40 deg. Celsius. The water is then removed under reduced pressure at 110 deg. Celsius until the water content is less than 0.1%. The product 5 has a hydroxyl value of 150 mg KOHg$^{-1}$, a water content of 0.02% and a viscosity of 305 centistokes.

EXAMPLE A

A polyol blend consisting of 100 parts of a sorbitol based polyol of hydroxyl value 490 mgKOH/g, 15 parts of a fire retardant based on tris(beta-chloroisopropyl)-phosphate, 2.5 parts of a catalyst based on N,N dimethylcyclohexylamine, 1.5 part of water, 1.5 parts of a oxyalkylene block copolymer surfactant, 0.1 part of alpha methyl styrene and 42.5 parts of 'Arcton' 11 fluorocarbon, was reacted with 148.9 parts of 'Suprasec' DNR methylene diphenyl diisocyanate ('Arcton' and 'Suprasec' are trademarks of Imperial Chemical Industries PLC). The polyol and isocyanate components were mixed with a variable shear mixer. At low shear and hence low mixing efficiency the above system produced poor quality foam with both isocyanate rich and polyol rich areas and large cells. The addition, to the polyol blend, of 10 parts of the polyol product 1 a as described in example 1 and the commensurate increase in isocyanate amount to 153.4 parts in order to maintain the index and the increase in fluorocarbon Arcton A11 to 46.2 parts in order to maintain the blowing ratio, resulted in better mixing under low shear as exemplified by better quality foam and a decrease in the heterogeneity of the constituents and a decrease in the visible cell size.

EXAMPLE B

The addition, to the polyol blend used in example A, of 11.5 parts of the polyol product as described in example 1 c and the commensurate increase in isocyanate amount to 151.8 parts in order to maintain the index and the increase in fluorocarbon Arcton A11 to 46 parts in order to maintain the blowing ratio, resulted in better mixing under low shear as exemplified by better quality foam and a decrease in the heterogeneity of the constituents and a decrease in the visible cell size.

EXAMPLE C

The addition, to the polyol used in example A, of 10 parts of the polyol products as described in example 3 and the commensurate increase in isocyanate amount to 153.4 parts in order to maintain the index and the increase in fluorocarbon Arcton A11 to 46.2 parts in order to maintain the blowing ratio, resulted in better mixing under low shear as exemplified by better quality foam and a decrease in the heterogeneity of the constituents and a decrease in the visible cell size.

EXAMPLE D

A polyol blend consisting of 25 parts of a glycerol based polyol of hydroxyl value 540 mg KOH/g, 75 parts of a toluene diamine based polyol of hydroxyl value 390 mg KOH/g, 2 parts of a catalyst based on N,N-dimethylcyclohexylamine, 2 parts of water, 1.5 parts of a siloxane oxyalkylene block copolymer surfactant, and 37.5 parts of 'Arcton'11 (trademark) fluorocarbon, was reacted with 142.8 parts of 'Suprasec'DNR (trademark) polymeric MDI.

The polyol and isocyanate components were mixed with a variable shear mixer. At low shear the system as described produced poor quality foam. The addition of 10 parts of the polyol of example 1 a and the commensurate increase of isocyanate and fluorocarbon A 11 to 145.3 parts and 41 parts respectively, resulted in better mixing under low shear as exemplified by better quality foam. In addition a marked decrease in surface friability was observed in that the adhesion of the foam coverings were much enhanced.

EXAMPLE E

In addition to the polyol blend used in example D of 10 parts of the polyol of example 5 and the commensurate increase of isocyanate and fluorocarbon A11 to 145.3 parts and 41 parts respectively, resulted in better mixing under low shear as exemplified by better quality foam

EXAMPLE F

A polyol blend consisting of 53 parts of a sorbitol based polyol of hydroxyl value 555 mg KOH/g, 66 parts of a sucrose based polyol of hydroxyl value 440 mg KOH/g, 13 parts of a toluene diamine/alkanolamine based polyol of hydroxyl value 502 mg/KOH/g, 2.6 parts of water, 2.6 parts of a catalyst based on N,N-dimethylcyclohexylamine, 2.0 parts of a siloxane oxyalkylene block copolymeric surfactant and 50.4 parts of 'Arcton' 11 fluorocarbon (trademark), was reacted with 209 parts of 'Suprasec DNR' (trademark) polymeric MDI. As in the previous examples, at low shear bad quality foams were obtained. The addition of 9.7 parts of the polyol of the invention of examples 1a or 2 and the commensurate increase of the polyisocyanate and blowing agent to respectively 214.2 parts and 55.5 parts resulted in better mixing at low shear and hence better quality foam and reduction in the visible cell sizes.

EXAMPLE G

The addition to the polyol blend used in example F of 9.7 parts of the polyol of example 4 and the commensurate increase of the polyisocyanate and blowing agent to respectively 214.2 parts and 55.5 parts resulted in better mixing at low shear and better quality foams and reduction in the visible cell size.

EXAMPLE H

The addition to the polyol blend used in example F of 13.2 parts of the polyol of example 1 c and the commensurate increase of the polyisocyanate and blowing agent to respectively 211.5 parts and 55.5 parts resulted in better mixing a low shear and better quality foam and reduction in the visible cell sizes.

EXAMPLE I

A polyol blend consisting of 100 parts of a sucrose based polyol of hydroxyl value 440 mg KOH/g, 2 parts of water, 3 parts of a mixture of catalysts based on N,N-dimethylcyclohexylamine and bis(2-dimethylaminoethyl)ether, 2 parts of a mixture of siloxane oxyalkylene surfactants ('Tegostab' (trademark) B8404 and B1903, trademarks of Goldschmidt AG) and 37.6 parts of fluorocarbon 'Arcton' 11 (trademark) was reacted with 141.8 parts of 'Suprasec' (trademark) DNR polymeric MDI. As in the previous examples, at low shear bad quality foams were obtained. The addition of 10 parts of the polyol of the invention of example 1 a or 3, and the commensurate increase of the polyisocyanate and blowing agent to respectively 141.9 parts and 39.9 parts resulted in better mixing at low shear and hence better quality foam and reduction in the visible cell size.

EXAMPLE J

A polyol blend consisting of 50 parts of a sucrose based polyol of hydroxyl value 310 mg KOHg$^{-1}$, 30 parts of a toluene diamine based polyol of hydroxyl value 390 mgKOHg$^{-1}$, 10 parts of glycerol based polyol of hydroxyl value 540 mgKOHg$^{-1}$, 10 parts of a glycerol based polyol of hydroxyl value 1120 mgKOHg$^{-1}$, 1.9 parts of water, 2.5 parts of a catalyst based on N,N-dimethylcyclohexylamine, 2.0 parts of a mixture of siloxane oxyalkylene block copolymeric surfactants and 31.9 parts of 'Arcton' 11 fluorobarcon (trade mark), was reacted with 135 parts of 'Suprasec DND' (trade mark) polymeric MDI.

As in the previous examples, at low shear bad quality foams were obtained. The addition of 10 parts of the polyol of the invention of example 1a and the commensurate increase of polyisocyanate and blowing agent to respectively 151.9 parts and 34.9 parts resulted in better mixing at low shear and hence better quality foam and reduction in the visible cell sizes.

We claim:

1. A polyether polyol having an average hydroxyl value in the range of 100 to 250 mgKOH/g which is an alkoxylated derivative of a polyhydric alcohol obtained as by-product in pentaerythritol manufacture and consisting essentially of a mixture of compounds according to formula (I)

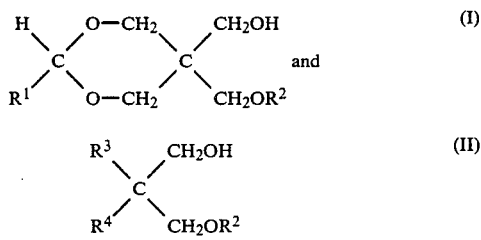

wherein
R$^1$ is H, CH$_3$ or OCH$_3$
R$^2$ is H, CH$_2$OH or CH$_2$ C(CH$_2$OH)$_3$
R$^3$ and R$^4$ which may be the same or different are H, CH$_2$OH, CH$_2$OCH$_3$ provided that only one of R$^3$ or R$_4$ may be CH$_2$OCH$_3$.

2. A polyether polyol in accordance with claim 1 wherein the alkoxylated derivative is a propoxylated derivative.

3. A polyether polyol blend comprising a polyether polyol according to claim 1.

4. A compatibilising additive comprising a polyether polyol according to claim 1.

5. A composition comprising 1 to 20 parts by weight of a polyether polyol according to claim 1 and 100 parts of a polyol blend.

6. A composition comprising 5 to 15 parts by weight of a polyether polyol according to claim 1 and 100 parts of a polyol blend.

7. A polyol blend comprising a polyether polyol according to claim 1 in addition to one or more catalysts, blowing agents, flame-retardant, surfactants, fillers and other usual ingredients used in polyurethane manufacture.

8. A process to manufacture rigid polyurethane foams comprising reacting a polyether and/or polyester polyol and a polyisocyanate in the presence of 1 to 20% parts by weight, for 100 parts of said polyether/or polyester polyol, of a polyether polyol according to claim 1.

9. A polyurethane product made according to the process of claim 8.

* * * * *